(12) United States Patent
Aurora et al.

(10) Patent No.: US 11,027,098 B2
(45) Date of Patent: Jun. 8, 2021

(54) CLIP FOR MEDICAL TUBING

(71) Applicant: Alexander Aurora, Joppa, MD (US)

(72) Inventors: Alexander Aurora, Joppa, MD (US);
Drew Harlacher, Delta, PA (US);
Cyrus Etemad-Moghadam, Fallston, MD (US); David C. Campbell, Bel Air, MD (US); Brian Ghezzi, Kingsville, MD (US); Samantha Verzi, Forest Hill, MD (US)

(73) Assignee: Alexander Aurora, Joppa, MD (US)

( * ) Notice: Subject to any disclaimer, the term of this patent is extended or adjusted under 35 U.S.C. 154(b) by 0 days.

(21) Appl. No.: 16/904,991

(22) Filed: Jun. 18, 2020

(65) Prior Publication Data

US 2020/0398027 A1   Dec. 24, 2020

Related U.S. Application Data

(60) Provisional application No. 62/865,121, filed on Jun. 21, 2019.

(51) Int. Cl.
*A61M 25/02* (2006.01)

(52) U.S. Cl.
CPC ....... *A61M 25/02* (2013.01); *A61M 2025/024* (2013.01)

(58) Field of Classification Search
CPC ... A61F 2002/30481; A61M 2025/024; A61M 39/00; A61M 2005/244; F16L 3/08; F16L 3/10; F16L 3/12; A47B 2088/4278
See application file for complete search history.

(56) References Cited

U.S. PATENT DOCUMENTS 6,631,538 B1 * 10/2003 Carr

* cited by examiner

*Primary Examiner* — Deanna K Hall
(74) *Attorney, Agent, or Firm* — Joseph E. Maenner; Maenner & Associates, LLC (57) ABSTRACT

A clip for medical tubing is a device for releasably and removably securing medical tubing, such as nasogastric tubes, surgical drainage tubes and the like, to a garment, such as a hospital gown or the like. The clip for medical tubing includes an elongated flexible member having longitudinally opposed first and second ends, and first and second clamps extending from the first and second ends, respectively, of the elongated flexible member. Each of the first and second clamps includes a yoke having first and second laterally opposed arms, at least two first resilient fingers extending in parallel from the first arm of the yoke, and at least one second resilient finger extending from the second arm of the yoke. The at least one second finger is resiliently compressible.

14 Claims, 10 Drawing Sheets

CLIP FOR MEDICAL TUBING

CROSS-REFERENCE TO RELATED APPLICATION

The present application claims priority from U.S. Provisional Patent Application Ser. No. 62/865,121, filed on Jun. 21, 2019, which is incorporated herein by reference in its entirety.

BACKGROUND OF THE INVENTION

Field of the Invention

The disclosure of the present patent application relates to clips, clamps, retainers and the like, and particularly to a clip for medical tubing that releasably secures the medical tubing to a patient's garment.

Description of the Related Art

Medical tubing, such as nasogastric tubes, surgical drainage tubes and the like, often must be secured to a patient's clothing to avoid dislodgement or patient injury. Current methods involve first applying tape to the tube, and then using a safety pin to fix the tape to the patient's clothing (e.g., a hospital gown). The tape can be problematic, in that it can be difficult to remove and also leaves an adhesive residue following removal. The safety pin presents clear concerns regarding patient safety. In addition to causing accidental injury to the patient, the safety pin can become dislodged, resulting in a small sharp object that can fall into the patient's bed, which may stab the patient or cause injury to unknowing staff caring for the patient. This metal device is also a risk and prohibitive to MRI imaging studies.

Although a wide variety of clamps exist for medical purposes, as well as for general hardware purposes, such clamps are typically either highly specialized (e.g., designed for one specific type of tubing, and made of one specific material in a single size) or are not easily adapted for the comfort and care necessary for retaining medical tubing to a patient. Thus, a clip for medical tubing solving the aforementioned problems is desired.

BRIEF SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The clip for medical tubing is a device for releasably and removably securing medical tubing, such as nasogastric tubes, surgical drainage tubes and the like, to a garment, such as a hospital gown or the like. The clip for medical tubing includes an elongated flexible member having longitudinally opposed first and second ends, and first and second clamps respectively extending from the first and second ends of the elongated flexible member. Each of the first and second clamps includes a yoke having first and second laterally opposed arms, at least two first resilient parallel fingers extending from the first arm of the yoke, and at least one second resilient finger extending from the second arm of the yoke, where the fingers are arcuate and have proximal portions curving toward the opposing arm or finger(s) and a distal end curling back away from the opposing arm or finger(s).

The tubing may be resiliently gripped by one clamp while the patient's gown is resiliently gripped by the clamp on the other end in order to retain the tubing out of the way. The clip for medical tubing may be formed of any suitable type of flexible material. For example, the clip for medical tubing may be manufactured from a thermoplastic elastomer using an overmolding injection process or the like. In an exemplary embodiment, plastic or a similar non-metallic substance is used, allowing the clip to be worn in a magnetic resonance imaging (MRI) machine.

In an alternative embodiment, first and second clamps, similar to those of the previous embodiment, are provided. Each of the first and second clamps has opposed first and second ends. A fixed end of a first elongated member is secured to the second end of the first clamp, and a free end thereof terminates in a ball. A fixed end of a second elongated member is secured to the second end of the second clamp, and a free end thereof terminates in a socket for releasably and rotatably receiving the ball of the first elongated member. An optional connector may be provided having a single socket for receiving the ball of the first clamp, and having a plurality of branches, each terminating in a respective ball, for engaging the sockets of multiple ones of second clamps. Alternatively, the connector may be provided with a single ball and a plurality of sockets, allowing for the reverse configuration.

In a further alternative embodiment, a plurality of clamps are provided, each being configured in a similar manner to those of the previous embodiments. A fixed end of an elongated member is secured to each clamp, and a free end of each elongated member terminates in both a ball and a socket. This arrangement allows the plurality of clamps to be releasably and pivotally connected to one another in a daisy chain arrangement.

In an additional alternative embodiment, first and second clamps, similar to those of the previous embodiments, are provided. Each of the first and second clamps has opposed first and second ends. A fixed end of a first elongated member is secured to the second end of the first clamp and, similarly, a fixed end of a second elongated member is secured to the second end of the second clamp. A flexible tube having opposed first and second open ends is further provided. The first open end is adapted for releasably receiving the free end of the first elongated member, and the second open end is adapted for releasably receiving the free end of the second elongated member. An optional connector may be provided having a first tubular member for receiving the free end of the first elongated member of the first clamp, and having a plurality of tubular branches for respectively receiving the free ends of multiple ones of second elongated members corresponding to multiple ones of second clamps. The optional connector may be formed from a relatively rigid material, with the first tubular member being positioned longitudinally opposite the plurality of tubular branches.

These and other features of the present disclosure will become readily apparent upon further review of the following specification and drawings.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

Similar reference characters denote corresponding features consistently throughout the attached drawings.

DETAILED DESCRIPTION OF THE INVENTION

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

The word "about" is used herein to include a value of +/−10 percent of the numerical value modified by the word "about" and the word "generally" is used herein to mean "without regard to particulars or exceptions."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Figure 1:
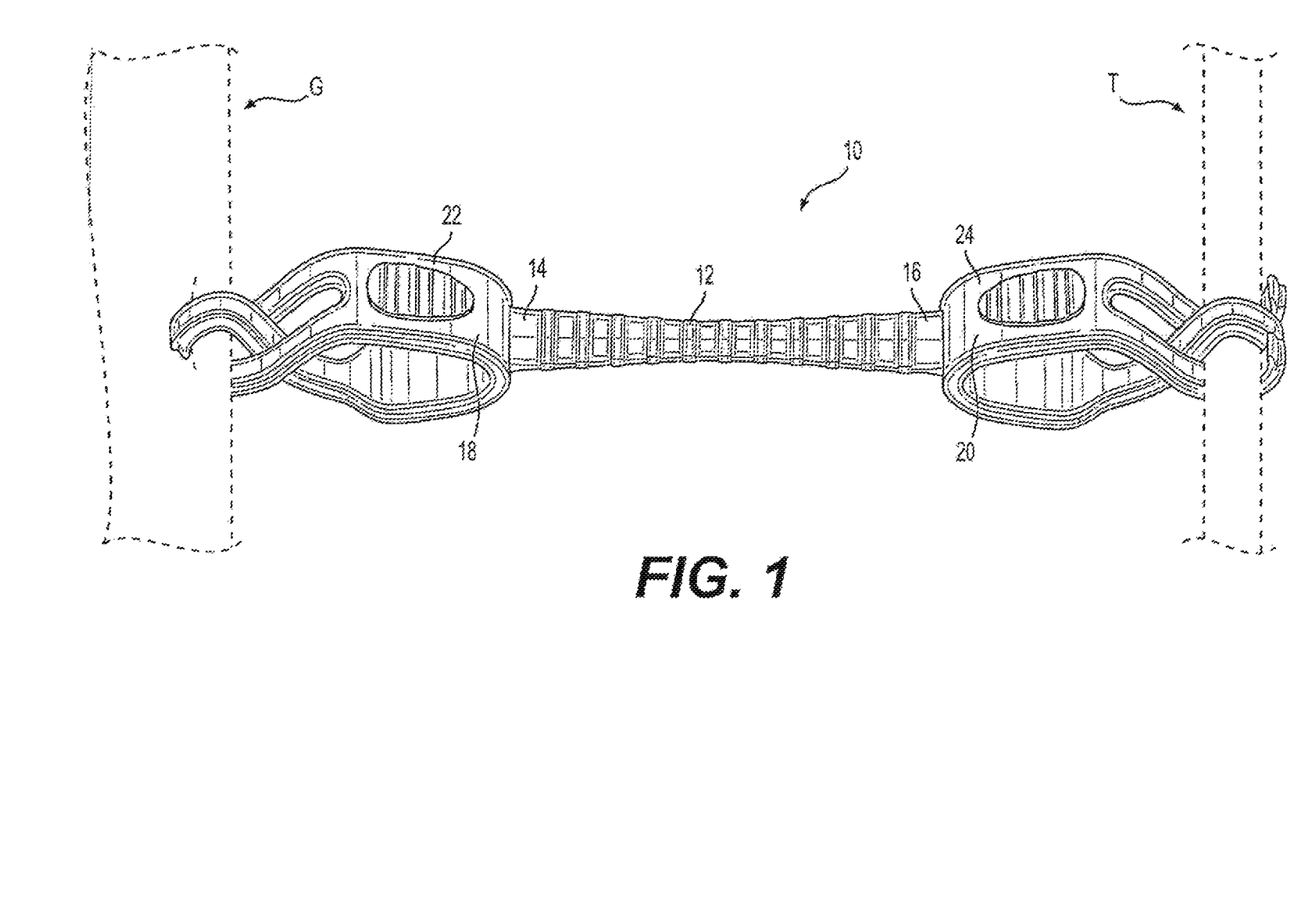
FIG. 1 is an environmental, perspective view of a clip for medical tubing.
Figure 2:
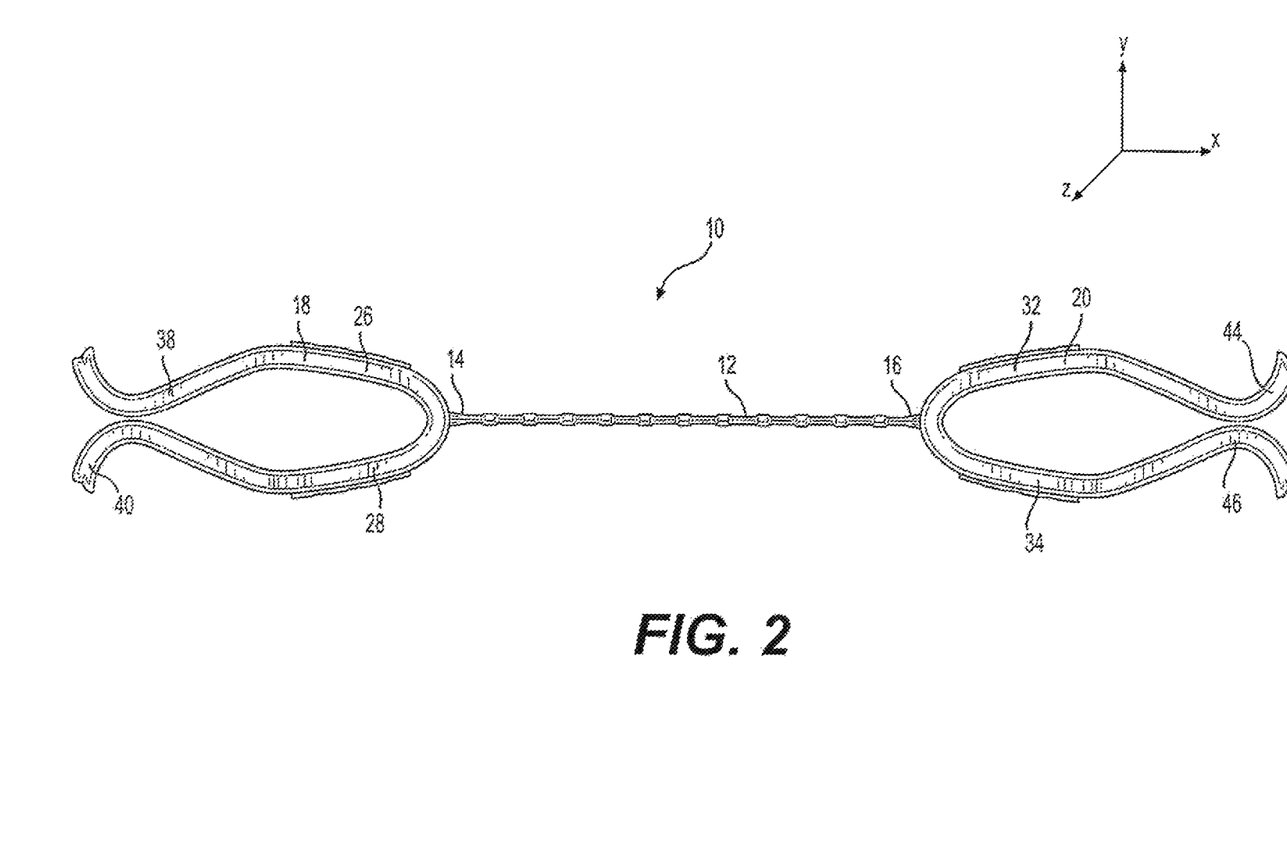
FIG. 2 is a side view of the clip of FIG. 1.
Figure 3:
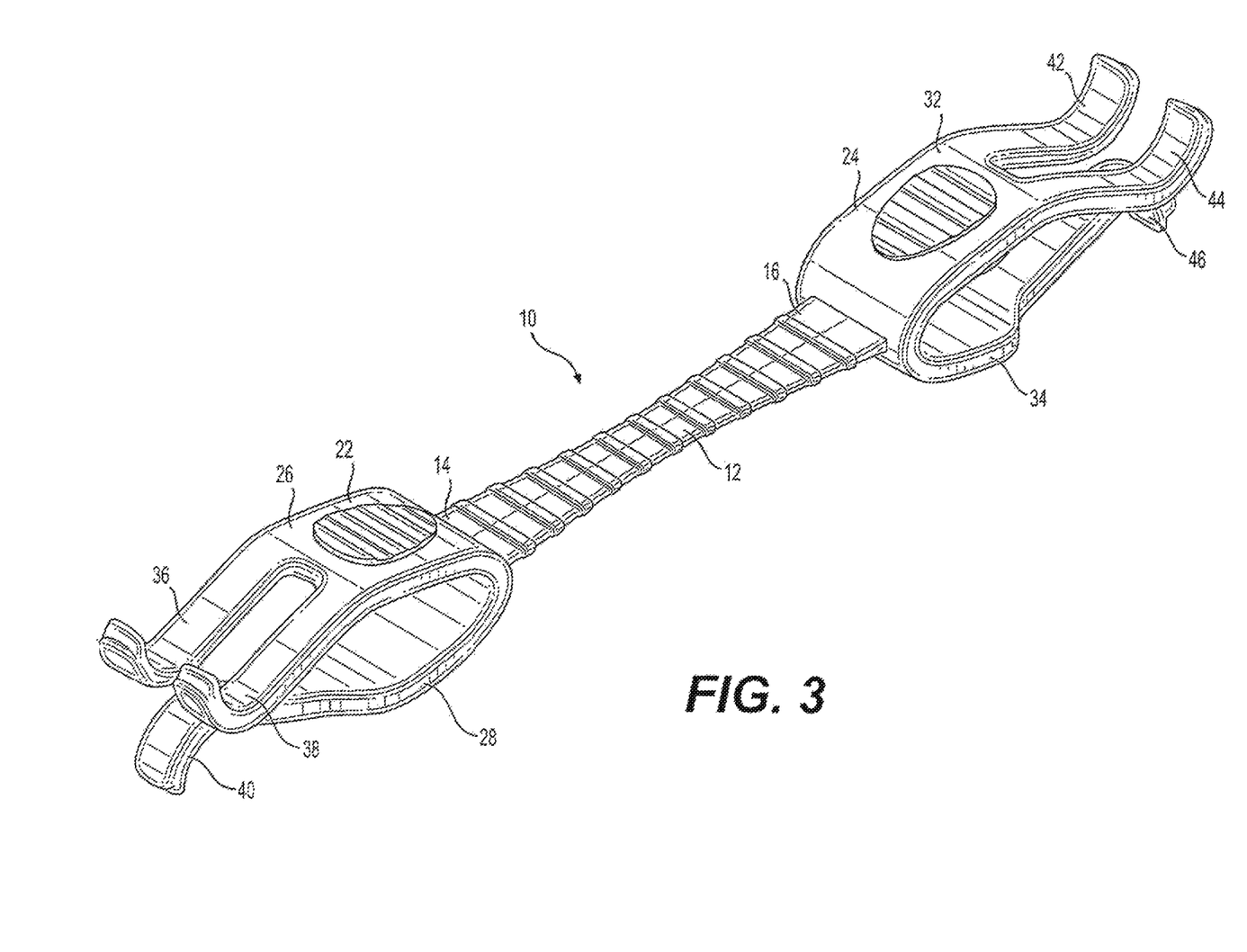
FIG. 3 is a perspective view of the clip of FIG. 1.
Figure 4:
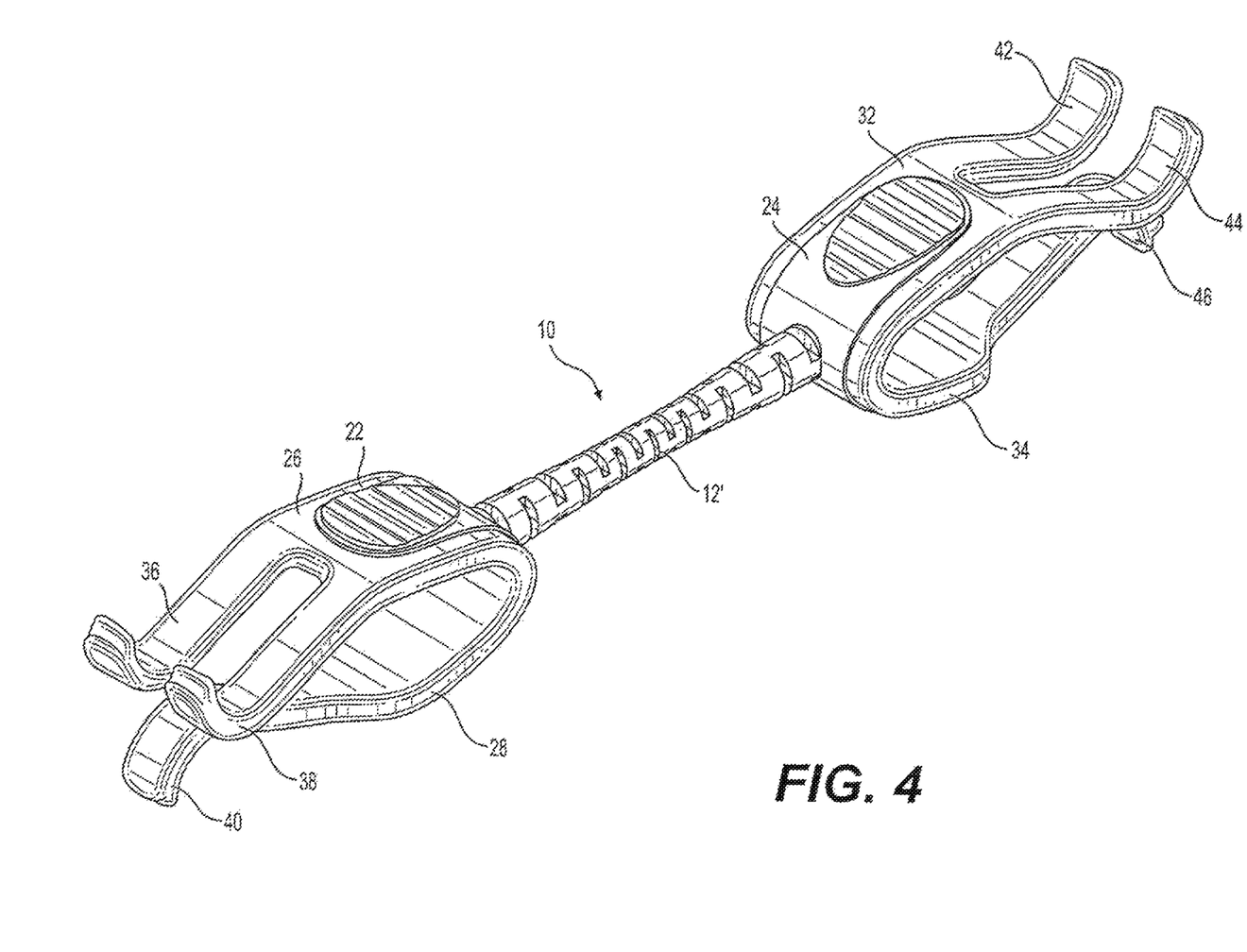
FIG. 4 is a perspective view of an alternative embodiment of a clip for medical tubing.

Referring to FIG. 1, the clip for medical tubing 10 is a device for releasably and removably securing medical tubing T, such as nasogastric tubes, surgical drainage tubes and the like, to a garment G, such as a hospital gown or the like. It should be understood that the garment G and the tubing T in FIG. 1 are shown for exemplary purposes only. As shown in FIGS. 2 and 3, the clip for medical tubing 10 includes an elongated flexible member 12 having longitudinally opposed first and second ends 14, 16, respectively, and first and second clamps 18, 20 respectively extending from the first and second ends 14, 16 of the elongated flexible member 12. The elongated flexible member 12 extends longitudinally (along the x-axis of FIG. 2) and may be formed of any suitable type of flexible material. For example, the elongated flexible member 12 may be manufactured from a thermoplastic elastomer using an overmolding injection process or the like (i.e., the clamps 18, 20 may be first molded as two separate pieces, and then the elongated flexible member 12 may be attached to the two clamps 18, 20 by overmolding a U-shaped plastic junction over the base of each clamp 18, 20, resulting in a one-piece clip 10). Preferably, plastic or a similar non-metallic substance is used, allowing the clip 10 to be worn in a magnetic resonance imaging (MRI) machine. It should be further understood that the configuration, relative dimensions and overall appearance of elongated flexible member 12 is shown in FIGS. 1-3 for exemplary purposes only. As an additional example, FIG. 4 shows the clip for medical tubing 10 with an alternative elongated flexible member 12' having the same function, but with different relative dimensions and overall configuration, and having alternating cutouts spaced along the length of member 12'.

As best shown in FIGS. 2 and 3, each of the first and second clamps 18, 20, respectively, includes a yoke 22, 24. As shown, each of yokes 22, 24 may be substantially U-shaped. Yoke 22 has first and second arms 26, 28, and yoke 24 has first and second arms 32, 34, respectively. At least two first resilient fingers 36, 38 extend in parallel from the first arm 26 of yoke 22, and at least one second resilient finger 40 extends from the second arm 28 of yoke 22. As shown, each of the fingers 36 and 38 has a proximal portion curving towards the opposing finger 40 and a distal end curving away from the opposing finger 40, while finger 40 has a proximal portion curving towards opposing fingers 36, 38 and a distal end curving away from the opposing fingers 36, 38. Finger 40 is spaced between fingers 36 and 38.

Yoke 24 is substantially identical to yoke 22, i.e., at least two first resilient fingers 42, 44 extend in parallel from the first arm 32 of yoke 24, and at least one second resilient finger 46 extends from the second arm 34 of yoke 24. As shown, each of the fingers 42, 44 has a proximal portion curving towards the opposing finger 46 and a distal end curving away from the opposing finger 46, while finger 46 has a proximal portion curving towards opposing fingers 42, 44 and a distal end curving away from the opposing fingers 42, 44. Finger 46 is spaced between fingers 42 and 44.

In some applications, the arms 32 and 34 of yoke 24 may be pinched together to extend the distal end of the resilient finger 46 between the distal ends of fingers 42 and 44 and spread apart from fingers 42 and 44 enough to insert the medical tubing into the cylindrical passage defined by the arcuate distal ends of the fingers 42, 44, and 46, the resiliency of the fingers clamping the tubing between the arcuate distal ends to retain the tubing in the clip 10. The opposite yoke 22 may grip the patient's gown between the fingers 36, 38, and 40, with fingers 36 and 38 on one side of the gown and finger 40 on the opposite side of the gown, also as shown in FIG. 1.

It should be understood that yokes 22, 24, and fingers 36, 38, 40, 42, 44, 46 may be formed from any type of resilient material suitable and for use with medical tubing, as well as being comfortable and non-damaging for attachment to the patient's clothing or garment. For example, yokes 22, 24, and fingers 36, 38, 40, 42, 44, 46 may also be manufactured from a thermoplastic elastomer using an overmolding injection process or the like. Such materials are relatively low cost, allowing the clip for medical tubing 10 to be easily disposed of and/or replaced. In an exemplary embodiment, plastic or a similar non-metallic substance is used, allowing the clip for medical tubing to be worn in a magnetic resonance imaging (MRI) machine.

Figure 5A:
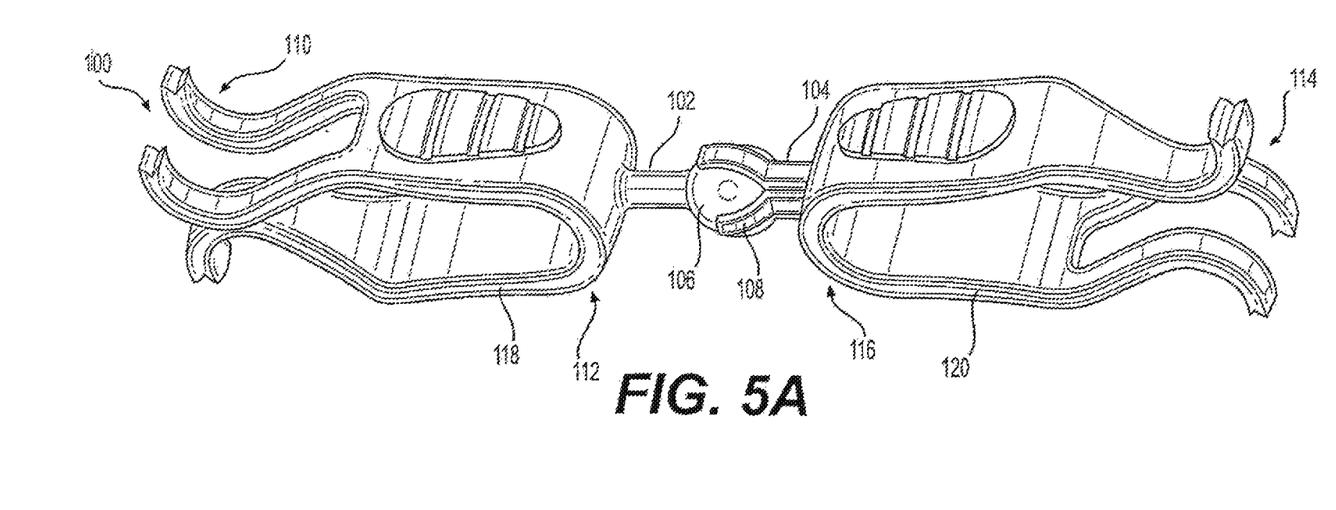
FIG. 5A is a perspective view of a further alternative embodiment of a clip for medical tubing.
Figure 5B:
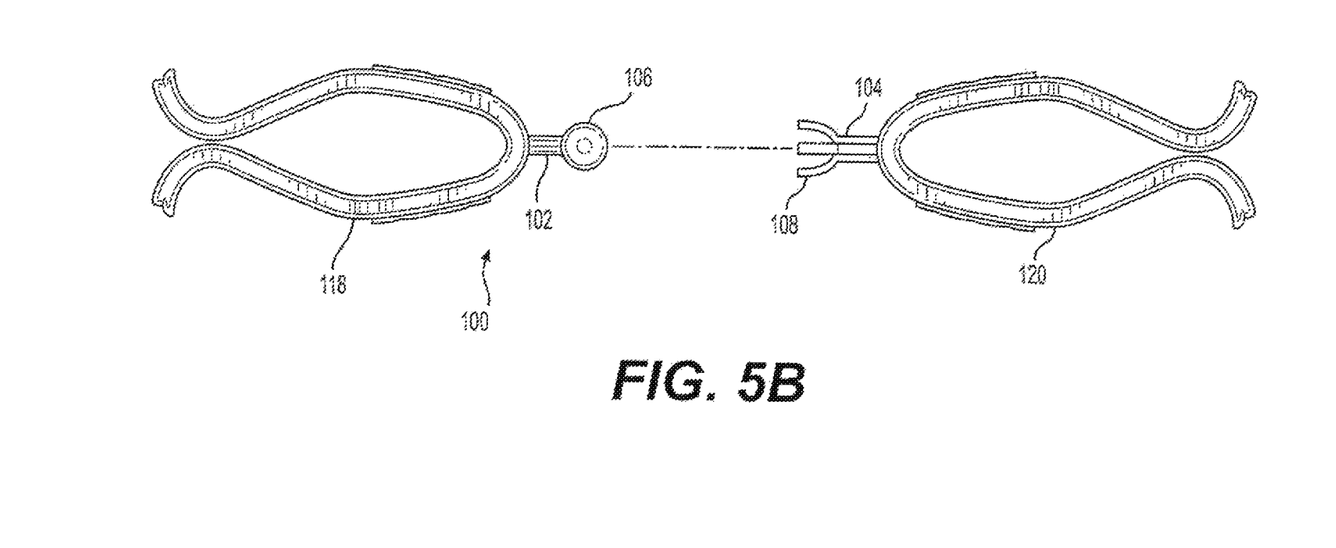
FIG. 5B is an exploded perspective view of the clip of FIG. 5A.

In the alternative embodiment of FIGS. 5A and 5B, the clip for medical tubing 100 includes first and second clamps 118, 120, respectively, which are similar in overall configuration to clamps 18, 20 of the previous embodiment. First clamp 118 has opposed first and second ends 110, 112, respectively, and second clamp 120 has opposed first and second ends 114, 116, respectively. A fixed end of a first elongated member 102 is secured to the second end 112 of the first clamp 118, and a free end thereof terminates in a ball 106. A fixed end of a second elongated member 104 is secured to the second end 116 of the second clamp 120, and a free end thereof terminates in a socket 108 for releasably and rotatably receiving the ball 106 of the first elongated member 102. It should be understood that the overall dimensions and configuration of elongated members 102, 104 are shown for exemplary purposes only. Similarly, it should be understood that the relative dimensions of the ball 106 are shown for exemplary purposes only. Further, it should be understood that the overall configuration of the socket 108 is shown for exemplary purposes only.

Figure 5C:
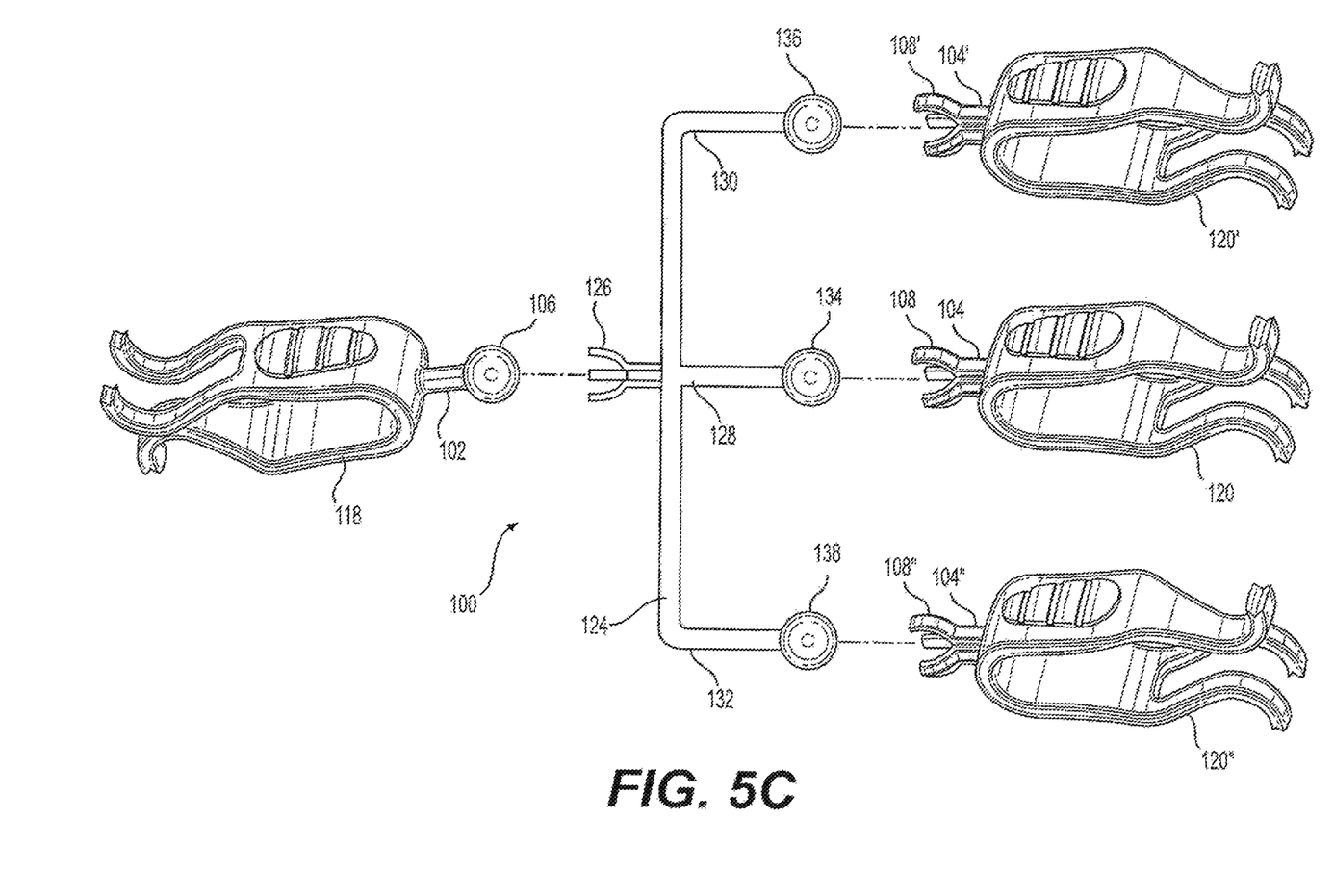
FIG. 5C is an exploded perspective view of the clip of FIG. 5A with an optional intermediate connector.

As shown in FIG. 5C, an optional intermediate connector 124 may be provided having a single socket 126 for receiving the ball 106 of the first clamp 118, and having a plurality of branches 128, 130, 132, each terminating in a respective ball 134, 136, 138, for engaging the sockets 108, 108', 108" of a plurality of second clamps 120, 120', 120". Alternatively, the connector 124 may be provided with a single ball and a plurality of sockets, allowing for the reverse configuration. It should be understood that although three such second clamps 120, 120', 120" and three corresponding branches 128, 130, 132 are shown for connector 124, connector 124 may be provided with any desired number of branches for connection to any desired number of second clamps. The clamps 120, 120', 120" may be oriented so that all three clamps 120, 120', 120" grip a single length of tubing at spaced intervals, or so that the three clamps 120, 120', 120" each grip a separate length of tubing in parallel.

Figure 6:
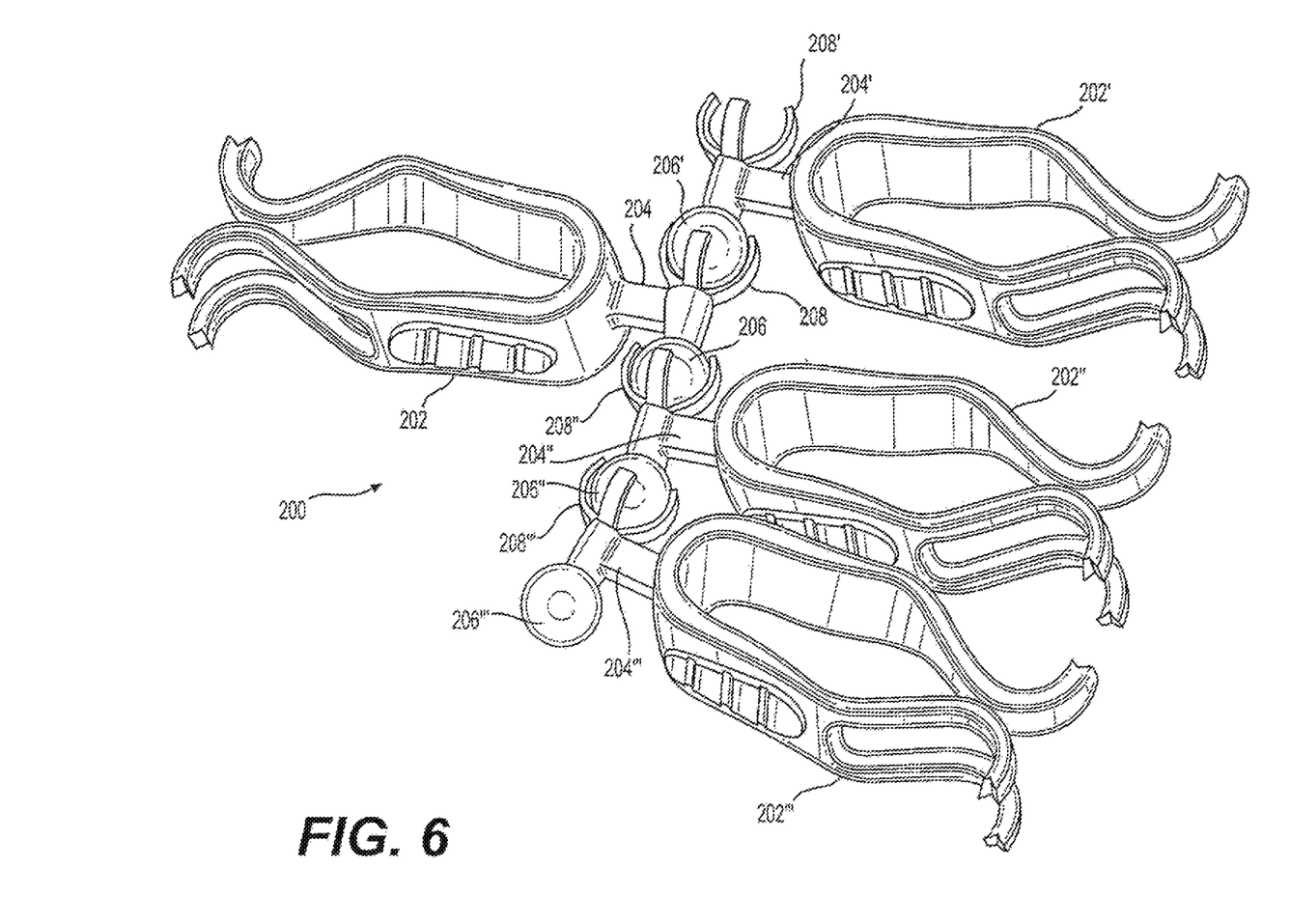
FIG. 6 is a perspective view of another alternative embodiment of a clip for medical tubing.

In the further alternative embodiment of FIG. 6, the clip for medical tubing 200 includes a plurality of clamps 202, 202', 202", 202''', each being configured in a similar manner to those of the previous embodiments. Although four such clamps are shown in FIG. 6, it should be understood that any desired number of clamps may be interconnected to one another. A fixed end of an elongated member 204, 204', 204", 204''' is secured to each clamp 202, 202', 202", 202''', respectively, and a free end of each elongated member 204, 204', 204", 204''' terminates in both a ball 206, 206', 206", 206''' and a socket 208, 208', 208", 208''', respectively. As shown, this arrangement allows the plurality of clamps 202, 202', 202", 202''' to be releasably and pivotally connected to one another in a daisy chain arrangement.

Figure 7A:
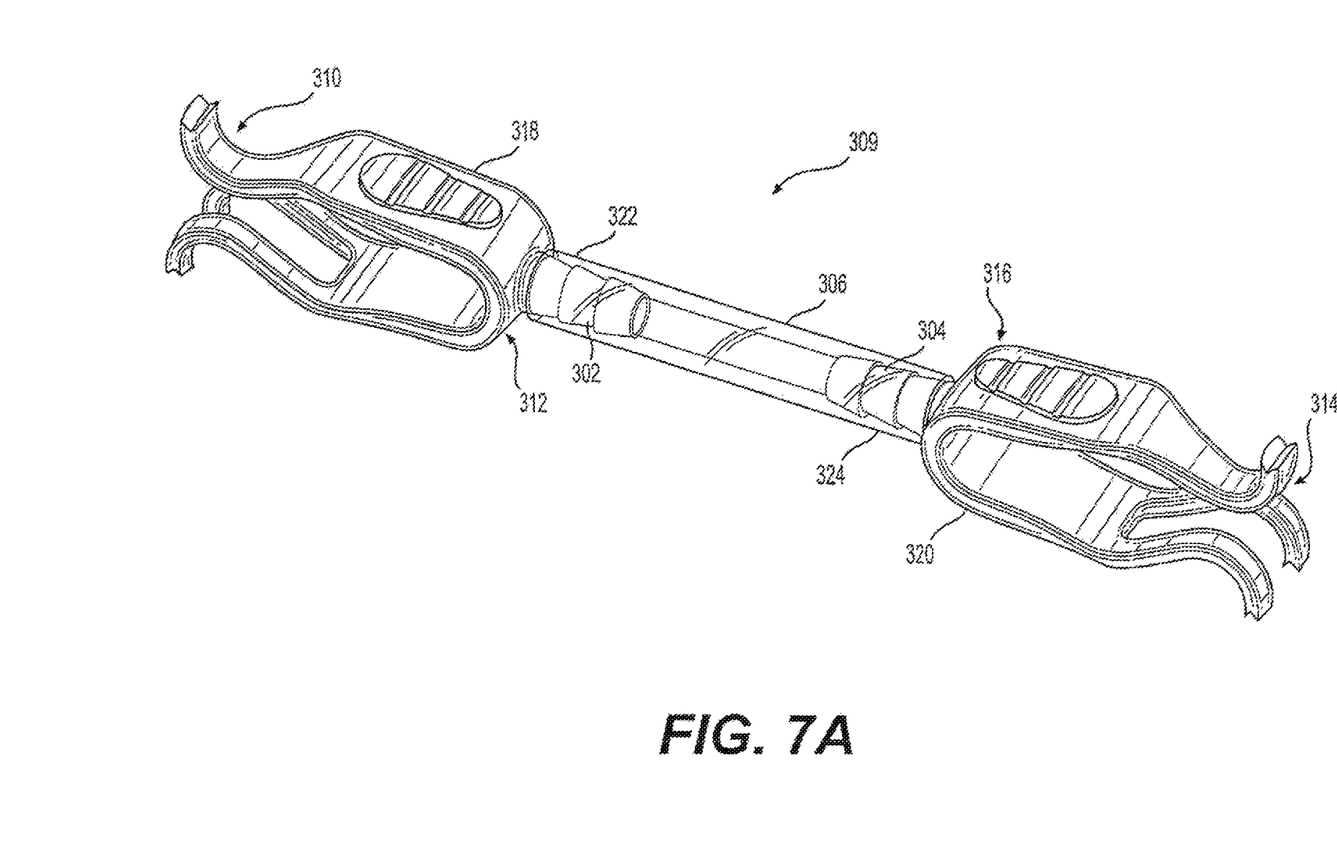
FIG. 7A is a perspective view of still another alternative embodiment of a clip for medical tubing.

In the additional alternative embodiment of FIG. 7A, the clip for medical tubing 300 includes first and second clamps 318, 320, respectively, which are similar in overall configuration to the clamps of the previous embodiments. First clamp 318 has opposed first and second ends 310, 312, respectively, and second clamp 320 has opposed first and second ends 314, 316, respectively. A fixed end of a first elongated member 302 (a barbed stub) is secured to the second end 312 of the first clamp 318, and a fixed end of a second elongated member 304 (a barbed stub) is secured to the second end 316 of the second clamp 320. A flexible tube 306 having opposed first and second open ends 322, 324, respectively, is further provided. The first open end 322 is adapted for releasably receiving a free end of the first elongated member 302, and the second open end 324 is adapted for releasably receiving a free end of the second elongated member 304. Although shown as transparent for exemplary purposes, it should be understood that flexible tube 306 may be alternatively opaque. Further, it should be understood that the dimensions and configuration of the first elongated member 302, the second elongated member 304, and the flexible tube 306 are shown for exemplary purposes only. Additionally, as shown, each of the first and second elongated members 302, 304 may be textured or contoured or barbed to frictionally engage the interior of the flexible tube 306, and also to aid in the insertion of the first and second elongated members 302, 304 within the flexible tube 306.

Figure 7B:
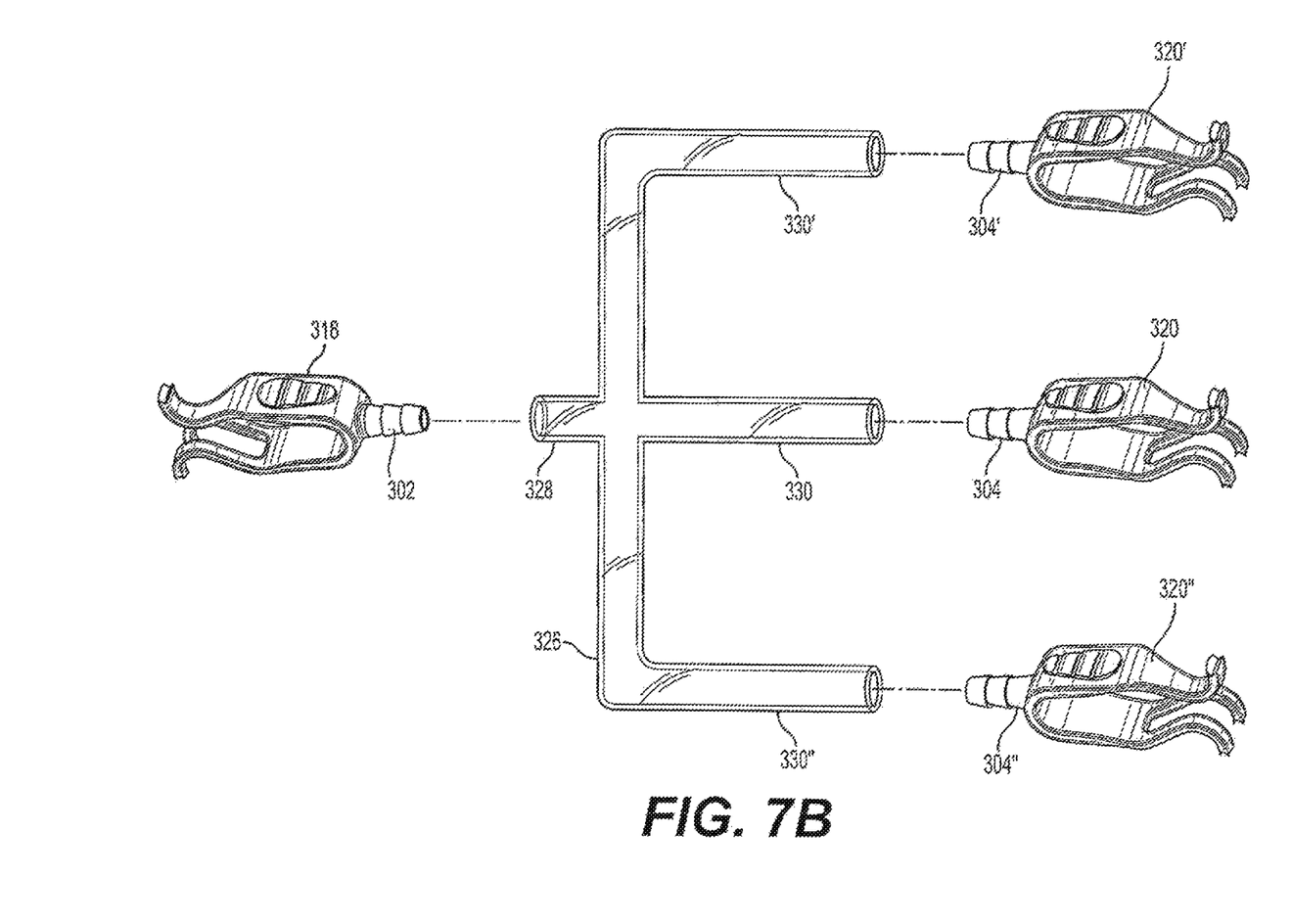
FIG. 7B is an exploded perspective view of the clip of FIG. 7A with an optional intermediate tubular connector.

As shown in FIG. 7B, an optional intermediate, multi-branch tubular connector 326 may be provided having a first tubular member 328 for receiving the free end of the first elongated member 302 of the first clamp 318, and having a plurality of tubular branches 330, 330', 330" for respectively receiving the free ends of multiple ones of second elongated members 304, 304', 304" corresponding to multiple ones of second clamps 320, 320', 320". It should be understood that although three such second clamps 320, 320', 320" and three corresponding branches 330, 330', 330" are shown for connector 326, connector 326 may be provided with any desired number of branches for connection to any desired number of second clamps. The optional connector 326 may be formed from a relatively rigid material, with, as shown, the first tubular member 328 positioned longitudinally opposite the plurality of tubular branches 330, 330', 330".

Figure 7C:
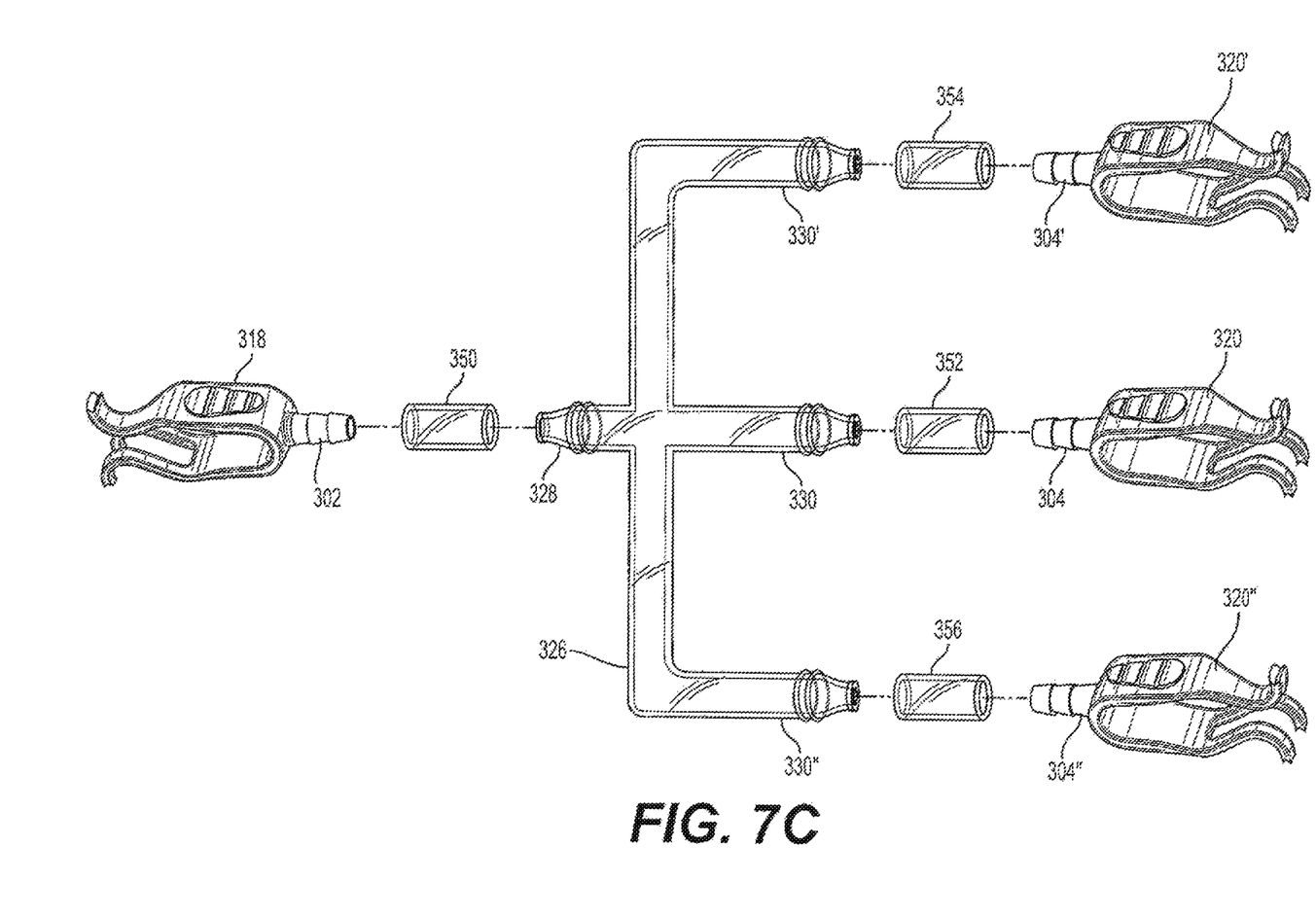
FIG. 7C is an exploded perspective view of a further alternative embodiment of the clip for medical tubing.

The alternative embodiment of FIG. 7C is similar to that of FIG. 7B, however, as shown, the connecting ends of the first tubular member 328 and the plurality of tubular branches 330, 330', 330" are each tapered or contoured, similar to the free end of the first elongated member 302 and the free ends of the second elongated members 304, 304', 304". This allows for the addition of one or more intermediate connector tubes 350, 352, 354, 356 to be used, increasing the adaptability of, and providing flexibility for the overall configuration of, the optional intermediate, multi-branch tubular connector 326.

It is to be understood that the clip for medical tubing is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A clip for medical tubing, comprising:
an elongated flexible member having opposed first and second ends; and
first and second one-piece clamps extending from the first and second ends of the elongated flexible member, respectively, each of the clamps having:
a yoke having first and second laterally opposed resilient arms;
at least two first resilient parallel fingers extending from the first arm of the yoke; and
at least one second resilient finger extending from the second arm of the yoke, wherein, in an unbiased position, each of the first fingers has a proximal portion curving towards the second finger and a distal end curving away from the second finger, the pair of first fingers and the second finger being compressible towards each other so that the second finger extends between the parallel first fingers, the first clamp being adapted for resiliently gripping medical tubing and the second clamp being adapted for resiliently gripping a support to keep the tubing clipped to the support.

2. The clip according to claim 1, wherein the elongate flexible member has a first wide portion proximate to the first clamp, a second wide portion proximate to the second clamp, and a narrow portion between the first and second wide portions.

3. The clip according to claim 1, wherein the elongate flexible member has a length between the first clamp and the second clamp, and wherein the elongate flexible member has alternating wide and narrow portions along the length.

4. The clip according to claim 1, wherein the first and second resilient parallel fingers each have a concave curvature and wherein the second resilient finger has a convex curvature.

5. The clip according to claim 1, wherein, in an uncompressed condition, the two first resilient parallel fingers extend on a first side of a plane and the second resilient finger extends on an opposing side of the plane.

6. A clip for medical tubing, comprising:
an elongated flexible member having opposed first and second ends; and
a first clamp extending from the first end of the elongated flexible member, the first clamp having a unitary body comprising:
a yoke having first and second laterally opposed resilient arms;
at least two first resilient parallel fingers extending from the first arm of the yoke; and
at least one second resilient finger extending from the second arm of the yoke, the first fingers and the second finger being compressible towards each other so that the second finger extends between the parallel first fingers, wherein, in an uncompressed condition, the two first resilient parallel fingers extend entirely on a first side of a plane and the at least one second resilient finger extends entirely on an opposing side of the plane, and wherein, in a compressed condition the at least two first resilient parallel fingers extend at least partially on the second side of the plane and the at least one second resilient finger extends on the first side of the plane such that, when the medical tubing is placed between the at least two first resilient parallel fingers and the at least one second resilient finger in the compressed condition, the at least two first resilient parallel fingers and the at least one second resilient finger releasably grip the medical tubing.

7. The clip according to claim 6, wherein the elongate flexible member has a first wide portion proximate to the first clamp, a second wide portion proximate to the second end, and a narrow portion between the first and second wide portions.

8. The clip according to claim 6, wherein the elongate flexible member has a length between the first clamp and the second end, and wherein the elongate flexible member has alternating wide and narrow portions along the length.

9. The clip according to claim 6, wherein the first and second resilient parallel fingers each have a concave curvature and wherein the second resilient finger has a convex curvature.

10. A clip for medical tubing, comprising:
an elongated flexible member having opposed first and second ends; and
first and second clamps extending from the first and second ends of the elongated flexible member, respectively, each of the clamps having:
a yoke having first and second laterally opposed resilient arms;
at least one first resilient finger extending from the first arm of the yoke on a first side of the elongated flexible member; and
at least one second resilient finger extending from the second arm of the yoke on a second side of the elongated flexible member, wherein, in an unbiased condition, the first resilient finger extends entirely on a first side of a plane and the second resilient finger extends entirely on an opposing side of the plane, and wherein, in a biased condition, the first resilient finger and the second finger are compressible towards and past each other so that a portion of the first finger extends on the opposing side of the plane and a portion of the second finger extends on the first side of the plane.

11. The clip according to claim 10, wherein the elongate flexible member has a first wide portion proximate to the first clamp, a second wide portion proximate to the second end, and a narrow portion between the first and second wide portions.

12. The clip according to claim 10, wherein the elongate flexible member has a length between the first clamp and the second end, and wherein the elongate flexible member has alternating wide and narrow portions along the length.

13. The clip according to claim 10, wherein the first resilient fingers each have a concave curvature.

14. The clip according to claim 10, wherein the elongated flexible member extends along the plane.

\* \* \* \* \*